United States Patent [19]

Hyman

[11] 4,285,468
[45] Aug. 25, 1981

[54] ARTICLE FOR THE DISPENSING OF VOLATILES

[76] Inventor: Sy Hyman, 425 E. 58th St., New York, N.Y. 10022

[21] Appl. No.: 37,688

[22] Filed: May 10, 1979

Related U.S. Application Data

[63] Continuation-in-part of Ser. No. 803,369, Jun. 3, 1977, Pat. No. 4,161,283.

[51] Int. Cl.³ .............................................. A61L 9/04
[52] U.S. Cl. ....................................................... 239/55
[58] Field of Search .................... 239/34, 36, 53–56

[56] References Cited

U.S. PATENT DOCUMENTS

| | | | |
|---|---|---|---|
| 3,578,545 | 5/1971 | Carson et al. | 239/53 |
| 3,623,659 | 11/1971 | Maierson et al. | 239/56 |
| 3,685,734 | 8/1972 | Paciorek et al. | 239/54 X |
| 3,785,556 | 1/1974 | Watkins | 239/56 X |
| 3,813,041 | 5/1974 | Kleine | 239/55 |
| 3,858,807 | 1/1975 | Rabussier et al. | 239/57 X |
| 3,896,995 | 7/1975 | Lelicoff | 239/56 X |
| 4,158,440 | 6/1979 | Sullivan et al. | 239/56 X |

FOREIGN PATENT DOCUMENTS 686329  3/1965  Italy ........................................... 239/56

*Primary Examiner*—Robert W. Saifer
*Attorney, Agent, or Firm*—Marvin Feldman; Stephen E. Feldman

[57] ABSTRACT

An article for the slow release of volatilizable substances, such as deodorizers, insecticides, repellants and the like, the article being formed from opposed outer and inner wall members joined along their peripheral portions to define a central reservoir portion for receiving and confining a volatile substance. The inner and outer wall member comprises a liquid non-porous but gas permeable flexible polymeric sheet material having an impermeable barrier layer releasably bonded to the outer surfaces thereof. In one embodiment the article is formed from a single strip folded and bonded to itself to form the reservoir. The barrier layer prevents escape of volatilized substance until its removal at the time of desired use. In a further aspect, a strippable adhesive layer is bonded to the outer surface of the second gas impermeable layer and removal of the stripable layer enables adhesive bonding of the article to environmental surfaces.

15 Claims, 14 Drawing Figures

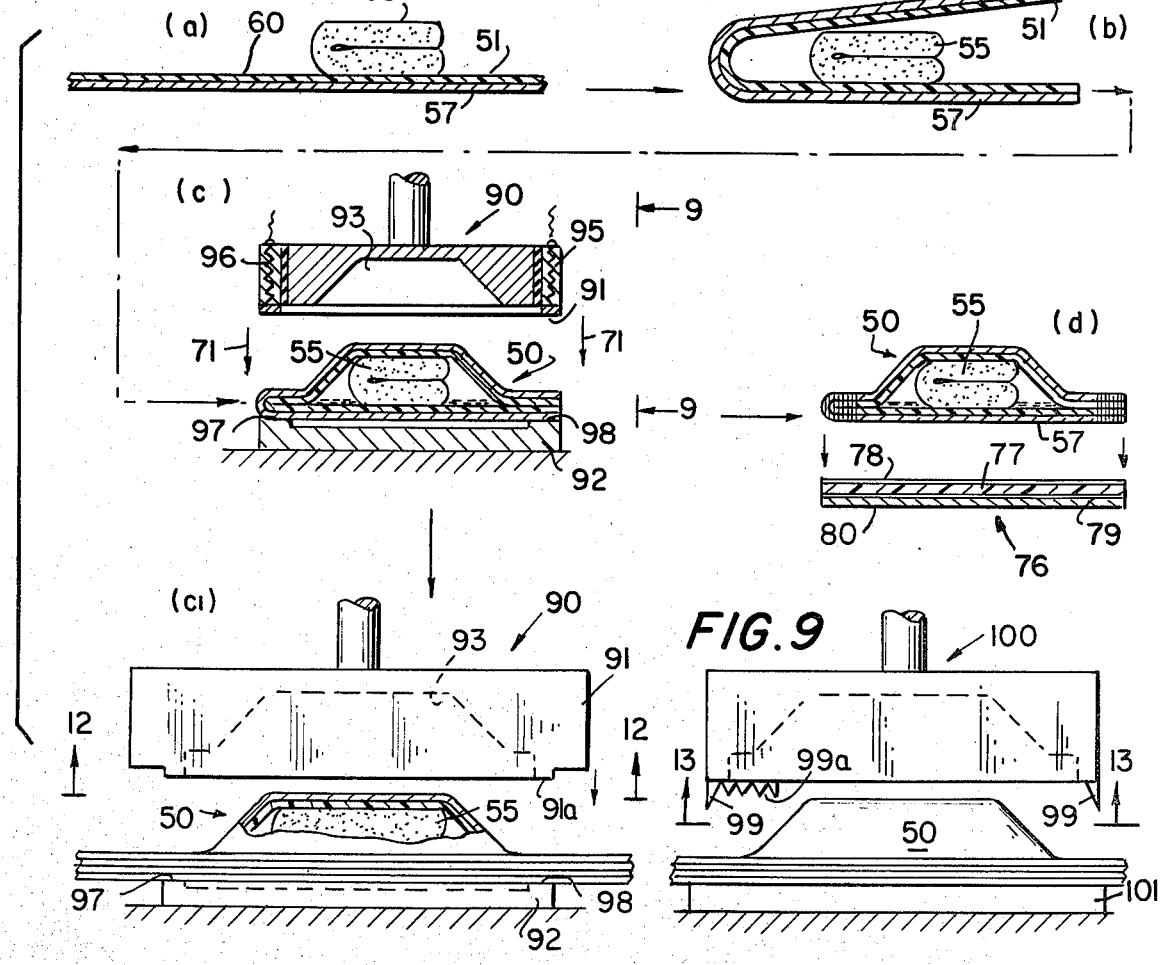

ARTICLE FOR THE DISPENSING OF VOLATILES

This application is a continuation-in-part of application Ser. No. 803,369, filed June 3, 1977, now U.S. Pat. No. 4,161,283.

BACKGROUND OF THE INVENTION

1. Field of the Invention

The invention relates generally to an article of manufacture for the slow release of a volatilized substance such as deodorizing means, insecticides, repellants, perfumes, medicaments and the like.

2. Description of the Prior Art

Articles of diverse types for the regulated, incremental release of a volatilizable substance over a period of time are well known in the art. Wick-type deodorizer dispensers having a stem portion retractably extensible from its container at the manipulation of the user to expose a fresh increment of volatile deodorizer as needed, and though effective under limited conditions, nevertheless entail objectionable aspects. Of somewhat bulky, awkward construction, such devices are usually difficult to manipulate and are accordingly highly visible in use, thus providing esthetically displeasing effects. Moreover, the impregnated wick is directly exposed to the surrounding moisture, heat and the like often leading to unpredictable and often unduly accelerated depletion rates. Envelope type or packet containers such as "towelettes" having a scented member disposed therein and likewise extensibly retractable to predetermined positions of projection are similarly objectionable. In either case, the whim of the user is the ultimate criteria for determining the rate and amount of scented vapor to be dispensed. As will be appreciated, unless the user manipulates the device as heretofore described, its intended effects are often virtually nullified. Pouch and box type dispensing means were more recently promulgated in the art, prove but partly remedial. In the case of the box type dispensers, the effective surface area available to pass vapor is limited since only the facing surface is exposed to the atmosphere. Moreover, these articles are likewise of rather bulky construction, difficult to manipulate and relatively costly to manufacture and assemble.

Representative prior art in this regard includes, for example, U.S. Pat. No. 3,575,345 which describes a deodorizer dispensing packet comprising opposed front and back sheets sealed together along their peripheral portions, each of the sheets preferably comprising an aluminum foil layer sandwiched between an inner polyethylene layer and an outer paper layer. Within the sealed enclosure is disposed an absorbent material, preferably porous paper impregnated with perfume. The packet is structurally adapted to be torn horizontally whereby to open the packet and enable withdrawal of the internally disposed impregnated porous paper for direct exposure to the surrounding atmosphere. An adhesive stripping is provided on one surface of the packet permitting its attachment to a suitable surface. Thus, the barrier foil layers are not removably attached and dispensing of the scented vapors is made possible only by tearing open the packet, the structure being so adapted. This device is thus similar to the "wick" type dispensers previously discussed hereinbefore.

U.S. Pat. No. 3,844,478 describes a block of deodorizing material such as a wax impregnated with a deodorizing substance. Removable protective coverings are provided on opposed surfaces of the block. An adhesive coating may also be provided on the rearward surface overcoated with the protective covering. A rigid plastic plate acting as a barrier may be interposed between the block and adhesive layer. This patent describes a rigid plastic cage structure in which having side and end walls and a foraminous surface through which vapors escape.

U.S. Pat. No. 3,815,828 describes a sealed envelope structure for containing liquid emulsions or impregnated pads for dispensing vapors to the atmosphere. In this patent, vapor release occurs through all surfaces of the envelope. Neither barrier layers nor adhesive means for attaching the envelope to a surface are described.

U.S. Pat. No. 3,702,677 describes a vapor dispensing device comprising a rupturable container containing a scented material disposed within a paper container. The device is activated by pressing the envelope in a manner to cause rupture of the internally disposed container. The paper container, being porous to liquids, allows the scented material to flow thereoutof.

Thus, a primary object of the invention is to provide an article for the slow dispensing of a volatilized substance wherein the foregoing and related disadvantages are eliminated or at least mitigated to a substantial extent.

Another object of the invention is to provide such an article capable of dispensing volatilized substance from a emanating liquid, solid, gel, saturated wad source, in regulated, linear quantities over a prolonged period of time.

Still another object of the invention is to provide such an article embodying structural features enabling efficient utilization of volatile substances and only at time of desired use.

A further object of the invention is to provide such an article wherein loss of volatilized substance through premature dispensing thereof is avoided before desired use and minimized in actual use.

It is another object of this invention to provide a slow vapor release article wherein there is a substantially a linear rate of release of the vapor to the surrounding atmosphere.

It is a further object of this invention to provide a slow vapor release article which effectively and efficiently utilizes each unit of vaporizable substance contained in the article.

A still further object of the invention is to provide such an article embodying structural features enabling its positioning on a variety of environmental surfaces.

Yet a still further object of the invention is to provide such an article having an arrangement of parts conducive to efficient mass production and relatively inexpensive manufacture.

Other objects and advantages of the invention will become more apparent hereinafter as the description proceeds.

Broadly speaking, the article of this invention is an outer layer of barrier material adhered to an inner layer of polymeric material. The layer is therewith bonded together along their peripheral portions to define a reservoir portion for containing a volatile substance. The barrier layer is releasably secured to the inner polymeric layer, whereby the volatile material is hermetically contained within the reservoir until a barrier is removed to permit the volatile material to diffuse through the polymeric material and volatilized from the exposed surface to the surrounding atmosphere. The polymeric material retains liquid but permits the diffusion of vapor of proportional quantities volatilizable material material to its outer surface from which it will volatilize.

In other words, the present invention provides an article for the controlled slow dispersion of a volatilizable substance to the surrounding atmosphere which comprises a sealed pouch joined along the periphery to define a substantially centrally disposed reservoir portion for containing a volatile substance, with the outer wall of the pouch comprising a substantially liquid impervious, gas permeable polymer and a barrier layer removably bonded to and completely covering the outer surface thereof, whereby the barrier layer prevents dispersion of volatilized vapors to the surrounding atmosphere until the barrier layer is removed from the polymer layer.

The invention is described but not limited by reference to the accompanying drawing wherein:

BRIEF DESCRIPTION OF THE DRAWINGS

FIG. 5 is a plan view with partly broken away section illustrating another embodiment of the invention;

FIG. 6 is a side elevational view of the folded side;

FIG. 7 is an enlarged sectional view taken along line 7—7 of FIG. 6; and FIG. 7A is an alternate embodiment;

FIGS. 8(a)-(e) is a schematic illustration of the process for making the latter embodiment of FIGS. 5-7 and 10;

FIG. 9 is a side view taken along line 9—9 of FIG. 8;

In the latter embodiment shown in FIGS. 5-10, it is a further object of the present invention to provide a slow vapor release article wherein single gas permeable polymeric material is employed in forming the reservoir and yet the aforesaid embodiments are achieved.

It is still a further object of this invention to provide an article as immediately aforesaid in which a solid pad provides the volatilizable liquid source, solid block, pellets or gels.

DETAILED DESCRIPTION OF THE INVENTION

Figure 1:
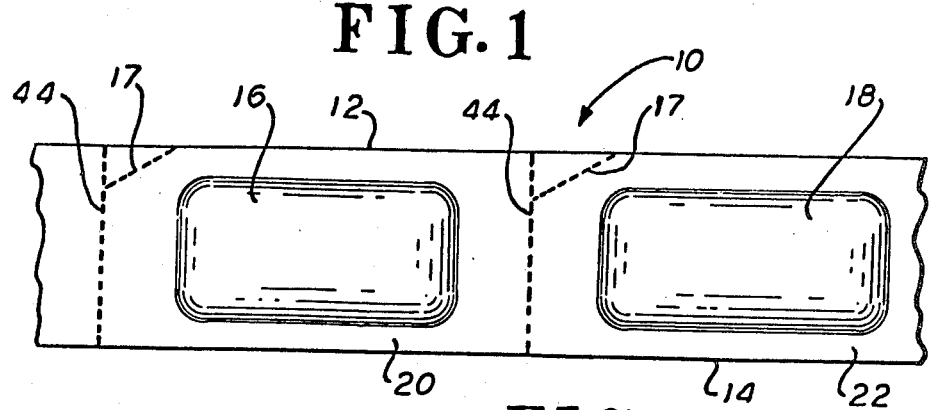
FIG. 1 is a top plan view shown partly broken away illustrating one embodiment of the invention.
Figure 2:
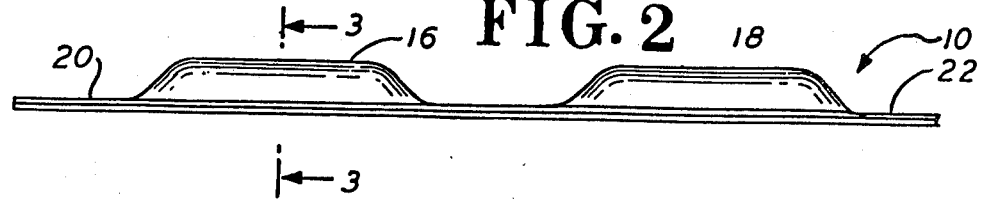
FIG. 2 is a side elevational view of the embodiment of FIG. 1.

In the following description like reference numerals designate similar parts throughout the several views and wherein 10 generally designates an article in accordance with the invention, the embodiment of FIG. 1 depicting an elongated strip material having opposed longitudinal edges 12 and 14 provided with pouch or envelope portions 16 and 18 surrounded by sealed rim portions 20 and 22, respectively. The construction is illustrated in more detail in FIG. 3. Outer wall member 24 comprises a first barrier layer 26 which completely overlies polymeric diffusion layer 28 being removably adhered thereto. Vapor barrier layer 26 may be of a variety of materials but is most preferably thin metal foil such as aluminum foil. It is essential in the present invention that vapor barrier layer 26 be impermeable to the passage of gas or vapor as will be described in detail hereinafter. Materials other than metal foil such as a wide variety of plastic materials, may be effectively used provided such material have the defined vapor impermeability characteristics and particularly within the temperature-humidity ranges encountered in the intended use. For example, as regards deodorizing applications in accordance with the invention, moderate temperatures normally characteristic of household applications would be encountered; however, in accordance with other embodiments of the invention e.g., the use of the article as a deodorizer, sanitizer, etc. to be added to the drying cycle of a clothes laundering operation, the temperatures would be quite higher. Thus, the chemical nature of barrier layer 26 depends on the ultimate utility contemplated, and selection of this material has necessary reference thereto.

Polymeric materials useful in the preparing diffusion layer 28 may be selected from a relatively wide range of substances, e.g., polymers and interpolymers derived the polymerization of one or more ethylenically unsaturated monomeric materials, i.e., the vinyl monomers. The polymeric materials are essentially water insoluble i.e., hydrophobic. In addition, such materials, in accordance with an essential aspect of the invention, while being of a impervious nature will nevertheless allow diffusion of the gas or vapor produced form the volatilization of the volatiled material confined within the reservoir 16. A particularly preferred polymer of the vinyl type is polyvinyl chloride although polyethylene, polypropylene and the like, may be used. Polymers other than those of the vinyl type may be used with advantage, these including, without necessary limitation, polyurethanes, polysiloxanes (silicones), thermoplastic elastomers, rubbers, etc. such as the product available commercially under the trade name designation HYTREL. As was the case with reference to barrier layer 26, selection of a given polymer within the limitations expressed is controlled at least in part by the conditions to be encountered in the ultimate use contemplated. The molecular weight of the polymer material may be considered in the selection of the diffusion layer. The thickness of polymer layer 28 will generally range between about 0.01 and 0.001 inch. In the case of metal foil, layer bonding thereof to polymer layer 28 may be achieved with adhesive; adhesive is also optional with the use of plastics as the barrier layer 26, the requisite bonding being obtainable, for example, by heat seal or heat fusion.

It is to be borne in mind that while the metal foil prevents vapor release to the atmosphere, some volatile fraction permeates the polymer diffusion layer and collects between the foil-polymer interface thereby separating and permitting more ready release of the foil from the polymer up to the heat-sealed perimeter of the reservoir.

For manufacturing convenience inner wall member 32 may be same as outer wall member 24 previously described. Alternatively, the inner wall may comprise only a single layer 34 which may be constructed of the same or different material as barrier layer 26. Again the essential properties of such barrier layer is both liquid and gas impermeable, in additional must be sealable to outer wall thereby completing formation of the sealed reservoir.

Barrier layer may be coated with an adhesive, preferably pressure sensitive, and an outer release paper. Alternatively, a section of double faced adhesive film and release paper may be applied, or tipped on during the reservoir forming, filling or sealing machine cycle.

Polymer diffusion layer 28 and barrier layer 34 are bonded to form a permanent union. This union is most effectively accomplished by heat-sealing or heat-fusion according to known techniques to form reservoir or supply portion 40 enclosed by rim portion 20. Reservoir portion 40 is adapted to contain and confine a volatile substance 42 which may be in liquid form, e.g. solution, gel, emulsion, suspension, etc., or alternatively may comprise a solid shape, pellets, or semi-solid material (not shown) such as wax, padding material and the like saturated or super-saturated with the volatile substance. Gel forms include blends of the liquid active volatile agents with gelling agents such as cab-o-sil, caringogen, carboxymethyl cellulose, and the like. Polymer layer 28 can be set to the partly arcuate shape illustrated in FIG. 3 e.g., by molding, or alternatively, can be a resiliently flexible member which assumes the shape illustrated upon introduction of the volatile substance.

Suitable volatile substances useful in the construction herein described include perfumes, deodorizers, fragrances, anti-bacterial agents, anti-microbial agents, counteractants, insecticides, insect-repellants, corrosion-inhibitors, attractants, medicants and the like. Suitable perfumes include without necessary limitation the essential oils of various fragrances, flower perfumes, e.g., lilacs, roses, etc., wood perfumes such as cedar, pine, briar, etc., fruit flavorings such as lemon, cherry, etc.

Medicinal volatiles include menthol, camphor, eucalyptus and the like; exemplary anti-bacterial agents include phenol, thymol, and the like.

In use, the consumer merely removes barrier layer 26 to "activate" the vapor dispensing article. For such purposes, a tab member 17 may be provided on layer 26. Removal of layer 26 allows the vapor from volatile substance 42 to escape into the surrounding atmosphere through permeable polymeric layer 28. The vapors are dispensed at a substantially linear rate and penetrate the entire extent of the reservoir surface area of layer 28. Premature or inadvertent dispensing of the vapors is effectively prevented by virtue of barrier layer 26. Thus, until the time of actual use, barrier layer 26 remains in place at which time removal is effected by the consumer. If desired, layer 26 can be repositioned on the polymer layer and the vapor diffusions discontinued until a later time.

In a further aspect of the invention, release layer 36 can also be stripped from the article as desired by the consumer to expose adhesive layer 38. This adhesive backing enables the article to be attached to a variety of environmental surfaces such as ables, closets, bathroom surfaces, etc. Moreover, being of flexible, lightweight construction, it can readily be affixed to surfaces of arcuate configuration such as piping. This adaptability feature enables the article to be positioned in areas which would not ordinarily be readily visible and is thus of significant advantage from an esthetic standpoint. The use of perfume-containing articles is of particular value where it is desired to mask or neutralize objectionable scents such as those encountered in kitchens, bathrooms, closets and the like. The article may also be used to dispense vapors having therapeutic effects when inhaled and can accordingly be affixed to any suitable surface in the room where necessary.

Figure 3:
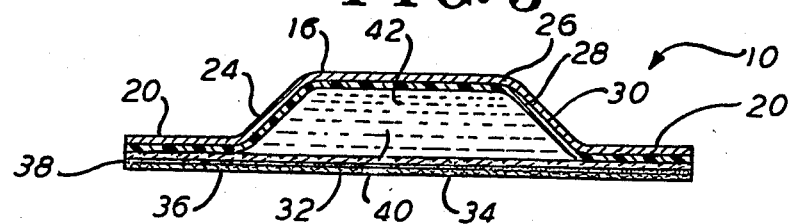
FIG. 3 is an end sectional view taken along line 3—3 in FIG. 2.

Handling of the present article is expedited by the presence of rim portion 20 (FIG. 3). Thus in use, the consumer need not directly contact pouch portion 16 and thus indirectly, the contents of reservoir portion 40. This is important since it virtually eliminates inadvertent rupturing of the pouch portions which might otherwise occur due to the compression force exerted in handling. As will be further noted, escape of the volatilized material is limited directionally, outwardly of the element through gas-permeable polymeric layer 28. Barrier layer 34 prohibits escape of such vapors rearwardly of the element. It is important that barrier layer 26 completely cover the outer reservoir surface of polymeric layer 28 so as to provide a seal. In this manner, premature escape of vapor is prevented.

As illustrated in FIG. 1, the article of the present invention may be provided in the form of an elongated strip comprising a plurality of such articles. Perforations 44 provided laterally of the connecting rim portions enable individual elements to be severed as desired. Alternatively, several connected elements can be used to provide an even greater supply of vapor to the surrounding atmosphere.

As previously mentioned, the volatile material may be in the form of a liquid, e.g., solution, suspension or emulsion, or in the form of a semi-solid or solid material impregnated with the volatile material. Thus, the emulsion form can be achieved with the use of a suitable solvent along with a surfactant material and/or a protective colloid such as polyvinyl alcohol, methyl cellulose and the like. Particularly effective surfactants include nonionic detergents derived from the polyoxyalkylation of alcohols. Impregnated waxes and fibrous materials may also be used. In any event, regardless of the type of carrier used, the volatile substance should readily produce vapor for passage through polymeric diffusion layer 28.

One of the particularly valuable aspects of the invention relates to the fact that a relatively large volume, and high concentration of aromatic perfume, for example, is accommodated by the article reservoir relative to its total size, e.g. 3–4 grams of perfume concentrate per article. In addition, an almost linear release of the perfume is achieved due to the constant concentration gradient of volatilizable material maintained within reservoir portion 40. This allows substantially uniform dispensing of the perfume ingredient over a prolonged period of use. This is to be contrasted with prior art devices and particularly those requiring adjustment on the part of the user as a given increment of available surface area sublimes and becomes depleted. Furthermore, the present articles are relatively inexpensive due to the simplicity of their construction, ease of continuous manufacture and the low cost types of polymeric material required.

In the present invention, the hermetically sealed envelope type construction renders the article highly efficient as regards the use of highly concentrated reservoir supply.

Figure 4:
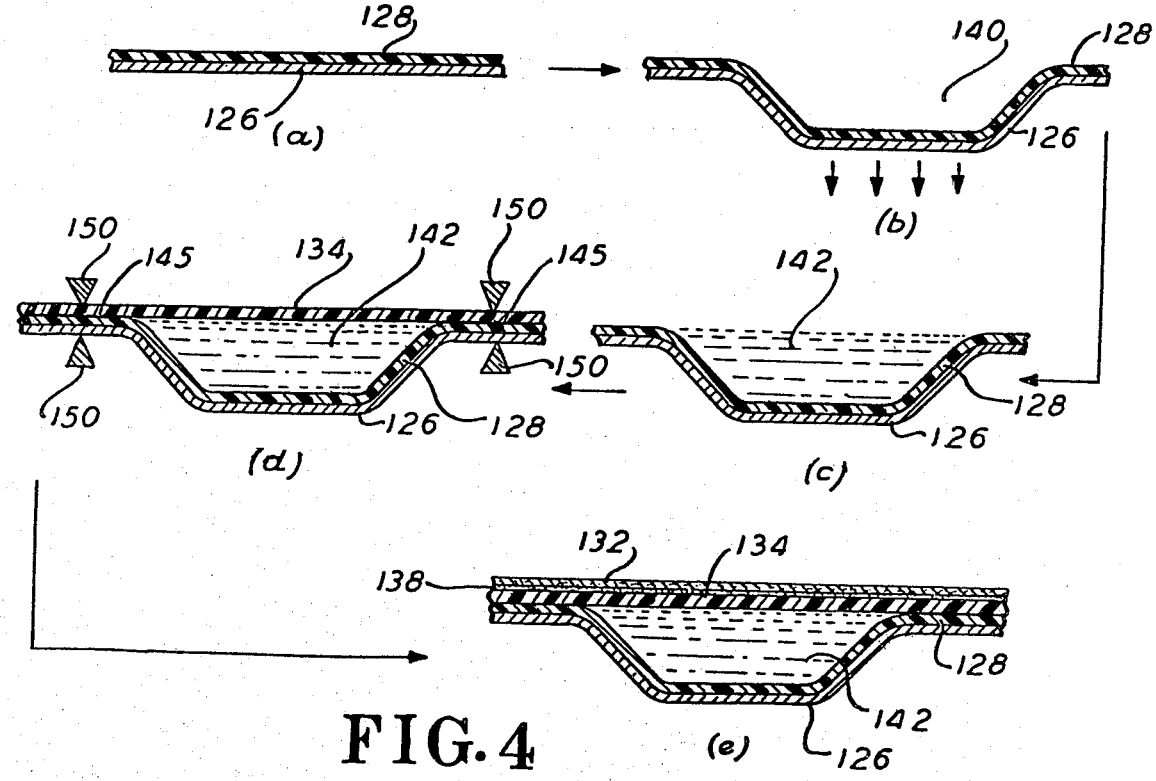
FIG. 4 is a process diagram depicting the step-wise method of forming the article of the invention.

Referring now to FIG. 4, there is shown a step-wise method of forming the article of the present invention. In step a., a continuous strip of the diffusion polymer 128 bonded to the metal foil 126 is provided with the metal foil disposed below the polymer, and in step b., a pouch or reservoir 140 is formed in the strip by well-known pressure-forming or vacuum forming means (not shown). In step c., the volatile substance (e.g. liquid) 142 is placed in formed reservoir 140. Thereafter a strip of polymer barrier layer 134 is placed over the reservoir portion as well as over the face portions 145 of polymer diffusion layer 128, and a well-known heat-seal crimp mechanism 150 provides a peripheral heat-seal of polymer layers 134 and 128, and a crimp-seal of layer 128 to foil 126. Turning to step c., the article of step d., is further provided with a pressure sensitive adhesive covered by release paper 132.

The present articles may be simply manufactured according to well-known techniques. As stated, bonding of polymeric layer 28 and barrier layer 34 can be effected by simple heat sealing or fusion. Volatile liquid substance can thereafter be introduced into reservoir portion 40 by needle injection. In the case of solid and semi-solid volatiles, fusion of layers 28 and 34 may be effected across the mass of volatile material. Other techniques relevant to preparation of the present articles are described for example in U.S. Pat. Nos. 2,940,230; 2,793,481; 2,290,564; 3,020,687; 2,958,169; 2,998,176; 2,469,975; 2,802,324; 3,065,915 and 636,317.

Referring to FIGS. 5-10 there is shown another embodiment of the invention generally referred to by numeral 50. Article 50 comprises a liquid impermeable gas permeable polymeric sheet 51 which is folded on itself and heat sealed at four portions, 52a, 51, 52 and 53 so as to form a liquid reservoir 54. A saturated fabric or paper pad 55 is disposed within the reservoir 54. An aluminum foil 57 has previously been adhesively bonded to the outer surface 58 of the polymer as at 59 and extends around the polymer. The volatilizable material, diffuses through the polymer 51 and renders the foil barrier layer more readily peeled and removed from the polymer layer to activate the article.

The article 50 is preferably formed as a strip 60 which contains a plurality of said articles 50. The strip contains a plurality of scores or perforations 61 which permit detachment of the individual articles 50 from each other. Each article also contains a partial oblique score 63, to provide a tab 62 for readily lifting the foil 57 in peeling same.

It is to be understood that the foil need only be peeled to the extent one would want to expose the polymer surface.

The more surface area exposed the more volatile material disperses to the atmosphere for the same time period.

Referring to FIG. 8, there is shown in FIGS. 8(a) to 8(d) a process schematic for forming the embodiment of FIGS. 5-7; and FIG. 8(e) refers to a further embodiment. In FIG. 8(a) there is shown the strip 60 in cross-section (end view) with aluminum foil 57 adhesively bonded thereto. Pad 55 is disposed on the polymer about one-quarter of the distance transversely across the polymer surface.

Figure 10:
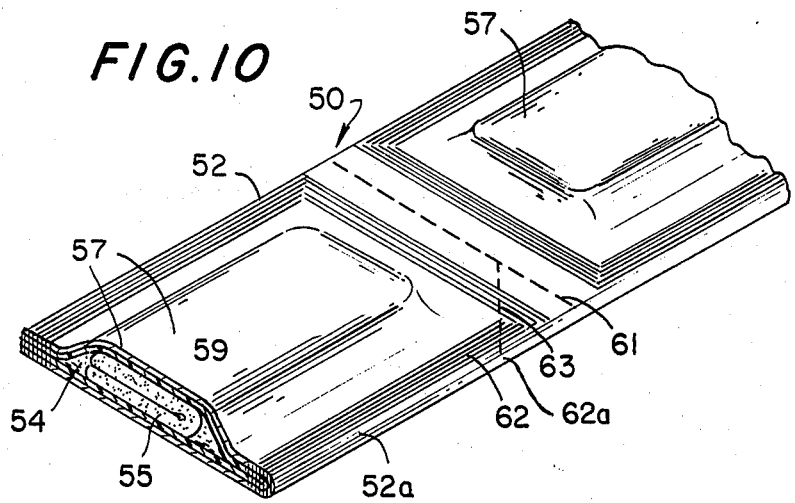
FIG. 10 is a sectional perspective view of the embodiment of FIGS. 5-7.
Figure 13:
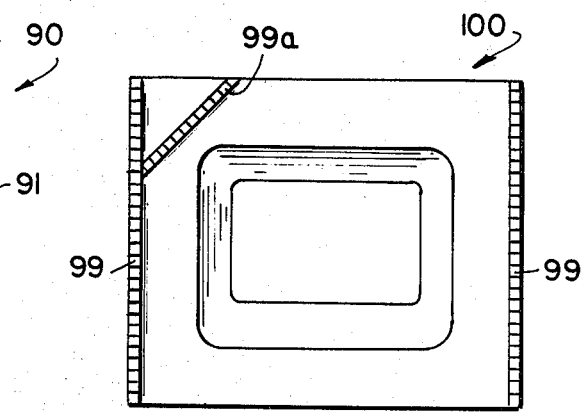

The polymer-foil sheet is then folded over to cover the pad as shown in FIG. 8(b). In-line heat-seal and perforating and scoring elements 90 and 100 respectively are well known in the art, and are applied as shown in FIGS. 8(c)-(c₁) and 8(d) respectively, so as to form sealed perforated portions 51, 52, 53 and 54 and scored portions 61 and 63. It is to be noted that transverse score 61 passes through the entire profile while oblique or tab score 63 does not, as best shown in FIG. 10. The partial (to 62a) score 63 permits ready peelaway of the barrier layers. The scores 61 and 63 are formed by score elements 99 and 99a, respectively (FIGS. 9 and 13). A score-receiver platen 101 is provided to facilitate scoring.

In further operation A, the article 50 may be further processed as shown in FIG. 9. Specifically, there is shown a double adhesive tape 76 comprising strip 77 with adhesives 78 and 79 on opposing surfaces, a peelable paper strip 80 covering adhesive 79 which tape may be adhesively or thermoadhesively bonded to the under surface 57. In this manner of construction the paper 80 may be peeled and the article 50 then applied to any desired surface.

FIG. 10 shows the completed embodiment of FIGS. 8a-8d and 9, in a cut-away perspective view showing pad 55 in liquid containing reservoir 54. Barrier layer 57 is shown with perforated cuts 61 and 63, with cut 63 being partial to 62a.

Specifically in forming the sealed article, a die 90 is provided which has vertically reciprocating top member 91 in relation to the feed strip, and a stationary bottom platen 92 or more specifically member 91 is formed with a recess 93 to accomodate the shape of the article. Member 91 is also formed with rectilinear peripheral electrical heat sealing elements (e.g. 95, 96) which are oppositely disposed to platen elements 97 and 98 so as to form the sealed portions 52a, 51, 52 and 53 in the article. As stated, in-line post-forming is made with perforation die cutter elements 99 and 99a of cutter 100 for forming perforations or scores 61 and the tab score 63 for tab 62; said scoring means being well-known in the art.

Referring to FIG. 7A, there is shown an alternate embodiment 150 wherein two separate polymeric and foil layers are heat sealed along four rectilinear lines, with seals 152a and 152 being shown. Thus, instead of a single polymer-foil sheet being folded over, two separate opposed polymer-foil strips (e.g. top polymer 159 and foil 157) are heat sealed to form reservoir 154 for pad 155 and its minimal liquid 156.

Figure 11:
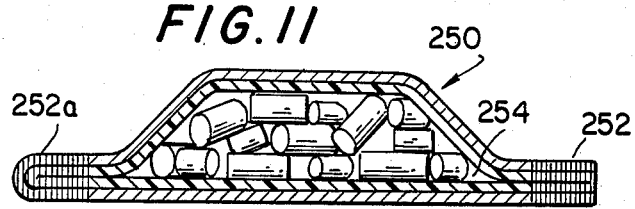
FIGS. 11 and 11A show another embodiment of the invention.
Figure 11A:
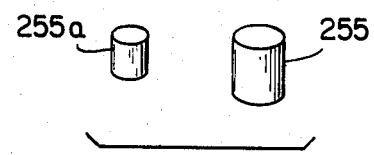
Figure 12:
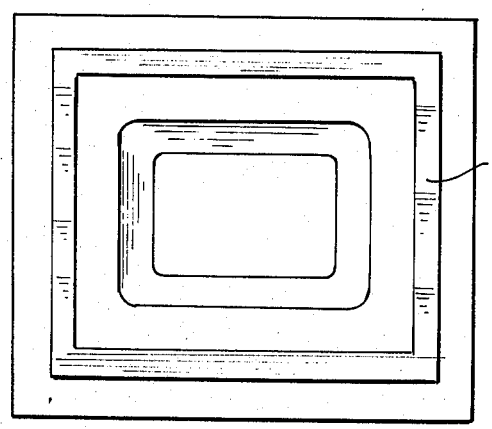
FIGS. 12 and 13 are bottom plan views of the heat-sealing and scoring elemens of FIGS. 8(c-c1) and 8(d) respectively.

Referring to FIGS. 11 and 11A, there is shown another embodiment 250 which comprises separate polymeric and foil layers heat sealed along four rectangular lines with seals 252 and 252a being shown, as is similar to that of FIG. 7A. The heat sealed reservoir 254 is similar in construction to that of 154 of FIG. 7A embodiment. However, the reservoir in this other embodiment contains solid pellets 255 and 255a. Pellets 255 and 255a are formed of a polymeric matrix (e.g. ethylene, vinyl acetate, polyvinyl chloride, polypropylene and the like) which matrix contains a predetermined concentration of volatilizable active agent.

It is to be noted that while cylindrical pellets 255 and 255a are shown, any solid-shaped particulates may be employed, including rods, spheres, flakes, powders and the like. The volatilizable active agent may be mixed with a polymeric matrix material and formed by extrusion or casting and converted to the desired size and shape as is well-known in the art.

The rate of release of volatilizable active agent from the polymer matrix can be predetermined by selecting polymer matrix composition, varying the concentration of active agent contained therein and varying the size (surface area) of the particulates.

It is also to be noted, pellets 255 and 255a are differently sized. Each pellet may contain a different active agent being released into the sealed reservoir at a predetermined rate. The combined vapors will move through the polymeric diffusion layer into the surrounding environment.

Great latitudes for achieving a programmed release of one or more volatilizable agents can be achieved by premixing or blending particulates containing active agents, and inserting a predetermined amount of active matrix into the reservoir of the dispenser.

The present invention has been described with respect to certain preferred embodiments thereof. However, it will be understood that changes and modifications may be made without departing from the scope thereof.

What is claimed is:

1. An article for the dispersion of a volatile substance to the surrounding atmosphere comprising a substantially liquid impervious, gas permeable polymeric layer, said layer being bonded so as to form a reservoir, a solid comprising a plurality of particulates comprising a polymeric matrix comprising a volatilizable substance in the matrix and being disposed in said reservoir, said matrix providing a controlled release of said volatilizable substance and being one selected from a varied concentration of said substance in said particulates and varied sized particulates, and a barrier removably adhesively attached to and covering the outer surface of said polymeric layer, whereby the volatilizable substance disperses from the particulates through the polymeric layer to the outer surface of the polymeric layer so that with the removal of the barrier layer the substance volatilizes from the exposed surface of the polymeric layer to the surrounding atmosphere.

2. The article of claim 1, wherein said barrier is a metal foil.

3. The article of claim 2 wherein said foil is aluminum.

4. An article according to claim 1 wherein said polymeric layer is selected from the thermoplastic group consisting of vinyl polymers, polyolefins, polyurethanes, elastomers, and silicones.

5. An article according to claim 4 wherein said polymeric layer comprises polyvinyl chloride.

6. An article according to claim 1 wherein said polymeric layer comprises a silicone polymer.

7. An article according to claim 1 wherein said volatile substance is one selected from the group consisting of perfumes, medicaments, insecticides and deodorants and germicidal agents.

8. An article according to claim 7 wherein said perfume is selected from the group consisting of essential oils, flower perfumes and fruit flavorings.

9. An article of manufacture comprising a plurality of said articles of claim 1 in the form of a unitary elongated strip, including laterally disposed perforations between said articles for expediting their removal from said strip, and wherein the barrier layer includes tab means for expediting removal of said layer from said article.

10. The article of claim 1, where said barrier layer and polymeric layer are pre-adhered and folded on itself and bonded at four portions to form said reservoir.

11. The article of claim 1, where there are two barrier layers and two polymeric layers pre-adhered and bonded to each other at four portions to form said reservoir.

12. An article for the dispersion of a volatile substance to the surrounding atmosphere comprising a substantially liquid impervious, gas permeable polymeric layer, said layer being bonded so as to form a reservoir, a solid comprising a plurality of particulates comprising a polymeric matrix comprising a volatilizable substance in the matrix and being disposed in said reservoir, said matrix providing a controlled release of said volatilizable substance and being one selected from a varied concentration of said substance and varied sized particulates, and a barrier removably adhesively attached to and covering the outer surface of said polymeric layer, whereby the volatilizable substance disperses through the polymeric layer to provide a liquid at the outer surface of the polymeric layer so as to attack and degrade the adhesive bond of the polymeric layer and barrier layer, so that said barrier layer is readily removale from the polymeric layer, and with the removal of the barrier layer the substance volatilizes from the exposed surface of the polymeric layer to the surrounding atmosphere.

13. The article of claim 12 wherein said particulates are formed as pellets.

14. The article of claim 12, wherein said polymeric matrix comprises at least one selected from the group of ethylene vinyl acetate, polyvinyl chloride, and polypropylene.

15. The article of claim 12 wherein some of said particulates contain a first volatilizable substance and other of said particulates contain a second volatilizable substance.

* * * * *